United States Patent [19]

Drake

[11] Patent Number: 5,118,900
[45] Date of Patent: Jun. 2, 1992

[54] CATALYST SUPPORTS, CATALYST SYSTEMS, AND OLEFIN DIMERIZATION

[75] Inventor: Charles A. Drake, Nowata, Okla.

[73] Assignee: Phillips Petroleum Company, Bartlesville, Okla.

[21] Appl. No.: 749,025

[22] Filed: Aug. 23, 1991

Related U.S. Application Data

[62] Division of Ser. No. 439,221, Nov. 20, 1989, Pat. No. 5,064,794.

[51] Int. Cl.$^5$ ............................................. C07C 2/24
[52] U.S. Cl. ..................................... 585/512; 585/510
[58] Field of Search ................................. 585/510, 512

[56] References Cited

U.S. PATENT DOCUMENTS

| | | | |
|---|---|---|---|
| 3,013,986 | 12/1961 | Castor | 502/79 |
| 3,364,135 | 1/1968 | Hansford | 502/79 |
| 3,403,975 | 10/1968 | Frilette et al. | 502/79 |
| 3,531,539 | 9/1970 | Tidwell | 260/677 |
| 3,660,516 | 5/1972 | Crain et al. | 260/683 D |
| 3,686,343 | 8/1972 | Bearden, Jr. et al. | 502/79 |
| 3,780,125 | 12/1973 | Takacs | 502/79 |
| 3,832,418 | 8/1974 | Bercik et al. | 260/683.15 R |
| 4,115,424 | 9/1978 | Umland et al. | 502/79 |
| 4,483,937 | 11/1984 | Liu | 502/79 |
| 4,559,320 | 12/1985 | Reusser | 502/251 |
| 4,628,138 | 12/1986 | Barnett et al. | 585/531 |

OTHER PUBLICATIONS

Kirk-Othmer, Encyclopedia of Chemical Technology (vol. 15) pp. 638–669 (1981).

Primary Examiner—Patrick P. Garvin
Assistant Examiner—E. D. Irzinski
Attorney, Agent, or Firm—Lynda S. Jolly

[57] ABSTRACT

Catalyst systems, methods for the preparation thereof, and olefin dimerization processes therewith are provided. Catalyst systems comprise at least one alkali metal hydroxide supported on a low-sodium, type Y zeolite.

20 Claims, No Drawings

CATALYST SUPPORTS, CATALYST SYSTEMS, AND OLEFIN DIMERIZATION

This application is a division of application Ser. No. 07/439,221, filed Nov. 20, 1989, now U.S. Pat. No. 5,064,794.

BACKGROUND OF THE INVENTION

This invention relates to zeolite supported alkali metal hydroxide catalysts.

Prior art discloses processes to dimerize olefins under somewhat harsh conditions, such as high temperatures, high pressures, and/or extreme product treatment, such as an acid pretreatment prior to product recovery. Furthermore, the catalysts used are not easy to prepare and low conversion and/or selectively rates are obtained.

The metathesis reaction diisobutylene and ethylene results in the production of neohexene and isobutylene. Isobutylene is a relatively common material. However, the diisobutylene starting material is not as readily available and is priced at 3 to 4 times the price of isobutylene. Obviously, a method to economically dimerize isobutylene and convert isobutylene to diisobutylene is desirable, especially if used in conjunction with the production of neohexane.

OBJECTS OF THE INVENTION

It is an object of this invention to provide an easily prepared, simple catalyst to dimerize olefins.

It is another object of this invention to provide a process to easily prepare a simple catalyst to dimerize olefins.

It is a further object of this invention to provide a process to dimerize olefins under mild conditions.

It is yet another object of this invention to dimerize olefins with high reactant conversion and high product selectivity.

It is yet a further object of this invention to provide a process to dimerize isobutylene to diisobutylene.

Therefore, in accordance with the present invention, the catalyst comprising an alkali metal hydroxide supported on a low sodium, faujasite or type Y zeolite can be used to dimerize olefins, such as isobutylene, under mild conditions.

DESCRIPTION OF THE PREFERRED EMBODIMENTS

The present invention provides a process to prepare a catalyst comprising an alkali metal hydroxide supported on the low sodium, faujasite or type Y zeolite. The resultant catalyst can be used to dimerize olefins, such as isobutylene to diisobutylene, under mild conditions with high reactant conversion and high product selectivity.

SUPPORTS

The catalyst support comprises a commercially available faujasite, a natural zeolite; or a synthetic faujasite, known as a type Y zeolite. Generally, these types of zeolites have a silicon/aluminum atom ratio within the range of about 2 to about 2.6, and preferably, within the range of about 2.15 to about 2.45. Additional information about zeolites can be found in the *Kirk-Othmer Encyclopedia of Chemical Technology*, Vol. 15, pp. 638–669 (1981), herein incorporated by reference. As used in this disclosure, the term "support" is not necessarily limited to a catalytically inert material. It is possible that the support contributes to the activity of the entire catalyst system.

A typical low sodium, type Y zeolite has a formula of $(NH_4)_{57}[(AlO_2)_{57}(SiO_2)_{135}] \cdot xH_2O$. This type of zeolite usually can be prepared from $Na_{57}[(AlO_2)_{57}(SiO_2)_{135}] \cdot xH_2O$ by replacing the sodium cations with $NH_4$ cations.

A typical faujasite has a formula of $Na_{59}[(AlO_2)_{59}(SiO_2)_{133}] \cdot 235H_2O$ and a typical type Y zeolite has a formula of $Na_{56}[(AlO_2)_{56}(SiO_2)_{136}] \cdot 250H_2O$. However, in order for the zeolite to be a support for this invention, it must be a low-sodium zeolite. Low-sodium zeolites usually have the sodium cations replaced by ammonium cations. This cation exchange, or replacement, can be effected by any method known in the art.

One exemplary commercially available low sodium, type Y zeolite is available from UOP, Hydrocracking and Custom Catalysts as LZ-Y82 ⅛". Typical physical properties of LZ-Y82 ⅛ are listed in Table I below.

TABLE I

| Extrudate Dimensions | |
|---|---|
| Diameter | ⅛ in. |
| Length | ⅛ to ½ in. |
| LOI at 1000° C. | 2.3 wt. % |
| Radial Crush Strength | 235 lbs. |
| Bulk Density | 37.9 lb/ft³ |
| Surface Area, 1 pt. BEP | 625 m²/g |
| Unit Cell Size | 24.45 Å |

Typical chemical properties of LZY-82 are listed in Table II below.

TABLE II

| | |
|---|---|
| $SiO_2$ | 65.6 wt. % |
| $Al_2O_3$ | 33.6 wt. % |
| $Na_2O$ | 0.15 wt. % |
| $Fe_2O_3$ | 0.18 wt. % |
| $CaO$ | 0.03 wt. % |

The zeolite preferably is in a particulate form, such as, but not limited to, granules, pellets, pills, and/or an extrudate. Usually, the particulate zeolite is within a size range of greater than about 200 mesh (0.84 mm) and most preferably within the size range of about 6 (3.36 mm) to about 14 (1.41 mm) mesh.

CATALYST PREPARATION

Catalyst systems employed in the practice of this invention comprise a low sodium, faujasite or type Y zeolite, described above, and at least one alkali metal hydroxide. It should be recognized, however, that the catalyst systems of the invention can contain additional components which do not adversely affect the catalyst performance, such as, for example, pigments, dyes, processing aids, inert fillers, and/or binders.

The alkali metal hydroxides contemplated to be within the scope of the invention include lithium hydroxide, sodium hydroxide, potassium hydroxide, rubidium hydroxide, and/or cesium hydroxide. Potassium hydroxide is the preferred alkali metal hydroxide because of best conversion and high product selectivity.

While the proportion of alkali metal hydroxide combined with the zeolite support can vary appreciably, generally at least about 1 weight percent of the alkali metal hydroxide based on the total weight of zeolite support will be employed. Generally, about 1 to about 25 weight percent is preferred. An alkali metal hydroxide loading of about 8 to about 14 weight percent based on the total weight of the zeolite support is most preferred for efficient use of reagents high catalyst activity and selectivity, and ease of preparation. Potassium hydroxide is the preferred alkali metal hydroxide due to its ready availability as well as ease and safety in handling.

The general procedure for preparation of the catalyst systems of the invention involves dissolving an alkali metal hydroxide in water and then adding the low sodium, type Y zeolite to the alkali metal hydroxide/water solution to form a slurry.

The contact time for the alkali metal hydroxide and zeolite support can be any time sufficient to thoroughly contact the alkali metal hydroxide and zeolite support. Usually times of about 1 minute to about 3 hours, preferably times of about 5 minutes to about 90 minutes, are used. Most preferably, contact times within the range of about 15 minutes to about 45 minutes are used to effect a thorough contacting.

The contacting conditions can be any conditions sufficient to affect adherence of the alkali metal hydroxide to the zeolite support. Any temperature and pressure are sufficient. Usually, for ease of use, ambient temperatures and ambient pressures are employed. The actual contacting of the alkali metal hydroxide in the zeolite support can merely be a soak. Agitation of the of the mixture can be done, so long as the zeolite particle size is not significantly reduced.

After completion of the contacting of the alkali metal hydroxide and zeolite support, the liquid can be removed according to any method known in the art. One exemplary method to remove liquid is to decant off any excess liquid off of the zeolite supported alkali metal hydroxide and then to dry the zeolite supported alkali metal hydroxide at a temperature below the decomposition temperature of any of the components under an inert atmosphere. Any drying temperature and time wherein substantially all water is removed is sufficient. For example, drying temperatures, wherein potassium hydroxide is the alkali metal hydroxide, can range from about 200° to about 550° C. and preferably within the range of about 300° to about 500° C. Drying time can vary, depending on drying the temperature and the alkali metal hydroxide used, however, times within the range of 30 minutes to about 20 hours can be used, preferably within the range of about one hour to about 5 hours.

The thus-dried catalyst system is maintained in an inert atmosphere, such as, for example, nitrogen or argon, until ready for further use.

Optionally, prior to use and/or charging the reactor, the catalyst system can be mixed with an inert substance to dilute the catalyst system and decrease the rate of olefin dimerization. Any inert substance which has no catalytic activity in an olefin dimerization reaction can be used. One example of such an inert substance is glass beads.

REACTANTS

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include both self-reaction and "co-dimerization" as defined above.

Suitable dimerizable olefinic compounds are those compounds having from about 3 to about 30 carbon atoms and having at least one olefinic double bond and at least on allylic hydrogen atoms, i.e., at least one hydrogen atom attached to carbon atoms adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof. The inventive catalyst is especially applicable for the dimerization of isobutylene to diisobutylene.

Suitable co-dimerizable olefin compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

REACTION CONDITIONS

The dimerization reaction of the invention can be carried out using either batch or continuous types of operation, although the catalysts of the invention, are particularly well suited for continuous, fixed bed, operation. Suitable equipment such as for example autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 10° to about 100° C. is suitable. Temperatures of 20° to about 60° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 20 to about 500 psig are employed, with pressures of about 50 to about 100 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (with would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors such as for example the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.5 to about 20 will be employed. A WHSV of about 0.5 to about 10 is preferred, with about 6.5 to about 5 WHSV most preferred for optimum catalyst productivity.

PRODUCTS

The olefinic products of the invention have established utility in a wide variety of application such as for example as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

EXAMPLE

In each of the following examples, typically, the dimerization of isobutylene was carried out in a steam heated 316 stainless steel tubular reactor ($\frac{1}{2}"\times 20"$). The catalyst system, bounded above and below by small volumes of glass beads, was combined with 20 grams of an inert substance, i.e., no dimerization catalytic activity, to dilute the catalyst system and thus reduce and control the reaction rate. The contents of the tubular reactor were maintained at room temperature, about 20° C., at about 100 psig and isobutylene was pumped into the reactor at a rate of about 60 mL/hr. After about 1 hour of reaction time and each one-half hour thereafter for the following 7 hours, a sample was collected and analyzed by gas liquid chromatography (GLC). The summarized results represent the analysis of the last dimerization sample collected.

The catalyst preparation procedure for the catalyst systems used in Runs 101-106 and 108-110 was to combine 20 g of LZ-Y82 $\frac{1}{8}"$ (LZ-Y82), size 6-14 mesh, available from UOP, Hydrocracking and Custom Catalysts, 50 ml water and the appropriate weight of alkali metal hydroxide, based on the weight of the LZ-Y82. The catalyst used in Run 107 was prepared in a similar manner as above, however 15 g of α-alumina/silica was used. Each solution was gently stirred to thoroughly contact the alkali metal hydroxide and the support material and then allowed to soak. After 30 minutes, excess liquid was decanted and the solid material was washed with two 50 ml portions of water. The catalyst used in Run 111 is available as Filtrol TM -24, from Englehard Minerals and Chemicals, Corp., in Newark, N.J. It is sold as an acid-washed, montmorilinite (an acid-washed, silica-alumina clay). Immediately prior to use, each catalyst was heated to 400° C. for 4 hours under a nitrogen purge and maintained under an inert atmosphere until use.

The dimerization results are summarized in Table I, wherein isobutylene (IB), diisobutylene-1 (2,4,4-trimethylpentene-1, DIB1), and diisobutylene-2 (2,4,4-trimethylpentene-2, DIB2) are listed. The results show that a catalyst system comprising an alkali metal hydroxide supported on a low sodium, faujasite or type-Y zeolite is an effective catalyst to dimerize olefins.

TABLE I

| Run | Catalyst System | IB | DIB1 | DIB2 | Heavies | DIB/IB |
|---|---|---|---|---|---|---|
| 101 | LZ-Y82 & 12.5% KOH | 30 | 46 | 7 | 17 | 1.77 |
| 102 | LZ-Y82 & 5% KOH | 62 | 14 | 2 | 22 | 0.26 |
| 103 | LZ-Y82 & 15% KOH | 93 | 3 | — | 4 | 0.03 |
| 104 | LZ-Y82 | 38 | 12 | 5 | 30 | 0.45 |
| 105 | LZ-Y82 & 10% LiOH | 38 | 27 | 6 | 29 | 0.87 |
| 106 | LZ-Y82 & 15% LiOH | 99 | 1 | — | — | 0.01 |
| 107* | Si Al & 0.6% KOH | 37 | 39 | 7 | 17 | 1.24 |
| 108* | LZ-Y82 & 7.5% CsOH | 48 | 26 | 4 | 21 | 0.63 |
| 109 | LZ-Y82 & 10% CsOH | 64 | 15 | 3 | 17 | 0.28 |
| 110 | LZ-Y82 & 15% CsOH | 60 | 16 | 4 | 21 | 0.33 |
| 111 | Fitrol -24 TM | 1 | 4 | 1 | 50 | — |

*2.5 g catalyst system used.

The Example has been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A dimerization process comprising contacting at least one olefin under dimerization conditions with a catalyst system comprising:

(a) a low sodium zeolite selected from the group consisting of faujasite, type Y, and mixtures thereof; and
(b) at least one alkali metal hydroxide;
wherein said alkali metal hydroxide is supported on said zeolite; and
wherein said alkali metal hydroxide is present within the range of about 1 to about 25 weight percent, based on the total weight of the zeolite; and
wherein substantially all water is removed.

2. A process according to claim 1 wherein said contacting is carried out at a temperature within a range of about 10° to about 100° C., a pressure of less than about 10,000 psig, and a weight hourly space velocity within a range of about 0.5 to about 20.

3. A process according to claim 1 wherein said zeolite has a silicon/aluminum atom ratio within a range of about 2 to about 2.6.

4. A process according to claim 1 wherein said zeolite is faujasite.

5. A process according to claim 1 wherein said zeolite is a type Y zeolite.

6. A process according to claim 5 wherein said type Y zeolite comprises 65.6 weight percent $SiO_2$, 33.6 weight percent $Al_2O_3$, 0.15 weight percent $Na_2O$, 0.18 weight percent $Fe_2O_3$, and 0.03 weight percent CaO.

7. A process according to claim 1 wherein said alkali metal hydroxide is selected from the group consisting of lithium hydroxide, sodium hydroxide, potassium hydroxide, rubidium hydroxide, cesium hydroxide, and mixtures thereof.

8. A process according to claim 7 wherein said alkali metal hydroxide is potassium hydroxide.

9. A process according to claim 1 wherein said olefin has from about 2 to about 30 carbon atoms per molecule.

10. A process according to claim 9 wherein said olefin is isobutylene.

11. A process for the production of diisobutylenes which comprises contacting isobutylene under dimerization conditions with a catalyst system comprising:
(a) a low sodium zeolite selected from the group consisting of faujasite, type Y, and mixtures thereof; and
(b) at least one alkali metal hydroxide;
wherein said alkali metal hydroxide is supported on said zeolite; and
wherein said alkali metal hydroxide is present within the range of about 1 to about 25 weight percent, based on the total weight of the zeolite; and
wherein substantially all water is removed.

12. A process according to claim 11 wherein said contacting is carried out at a temperature within a range of about 20° to about 60° C., a pressure within a range of about 50 to about 100 psig, and a weight hourly space velocity within a range of about 0.5 to about 10.

13. A process according to claim 11 wherein said zeolite has a silicon/aluminum atom ratio within a range of about 2 to about 2.6.

14. A process according to claim 11 wherein said zeolite is faujasite.

15. A process according to claim 11 wherein zeolite is a type Y zeolite.

16. A process according to claim 15 wherein said type Y zeolite comprises 65.6 weight percent $SiO_2$, 33.6 weight percent $Al_2O_3$, 0.15 weight percent $Na_2O$, 0.18 weight percent $Fe_2O_3$, and 0.03 weight percent CaO.

17. A process according to claim 11 wherein said alkali metal hydroxide is selected from the group consisting of lithium hydroxide, sodium hydroxide, potassium hydroxide, rubidium hydroxide, cesium hydroxide, and mixtures thereof.

18. A process according to claim 17 wherein said alkali metal hydroxide is potassium hydroxide.

19. A process according to claim 11 wherein said diisobutylene is selected from the group consisting of 2,4,4-trimethylpentene-1, 2,4,4-trimethylpentene-2, and mixtures thereof.

20. A process for the production of diisobutylenes which comprises contacting isobutylene under dimerization conditions with a catalyst system comprising:
(a) a type Y, low sodium zeolite; and
(b) potassium hydroxide;
wherein said alkali metal hydroxide is supported on said zeolite; and
wherein said alkali metal hydroxide is present within the range of about 1 to about 25 weight percent, based on the total weight of the zeolite; and
wherein substantially all water is removed.

* * * * *